(12) United States Patent
Heruth

(10) Patent No.: US 6,198,966 B1
(45) Date of Patent: Mar. 6, 2001

(54) RECIRCULATING IMPLANTABLE DRUG DELIVERY SYSTEM

(75) Inventor: Kenneth T. Heruth, Edina, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/258,527

(22) Filed: Feb. 26, 1999

(51) Int. Cl.[7] .................................................. A61K 9/22
(52) U.S. Cl. .......................................... 604/20; 604/890.1
(58) Field of Search .................................. 604/19, 20, 21, 604/30, 501, 503, 508, 65–67, 82–85, 186, 246, 257, 890.1–892.1

(56) References Cited

U.S. PATENT DOCUMENTS

| | | |
|---|---|---|
| 4,217,894 * | 8/1980 | Franetzki ........................ 128/213 R |
| 4,278,087 | 7/1981 | Theeuwes . |
| 4,290,426 | 9/1981 | Luschen et al. . |
| 4,320,759 | 3/1982 | Theeuwes et al. . |
| 4,327,725 | 5/1982 | Cortese et al. . |
| 4,576,604 | 3/1986 | Guittard et al. . |
| 4,608,048 | 8/1986 | Cortese et al. . |
| 4,615,698 | 10/1986 | Guittard et al. . |
| 4,627,850 | 12/1986 | Deters et al. . |
| 4,633,878 * | 1/1987 | Bombardieri ....................... 128/635 |
| 4,655,766 | 4/1987 | Theeuwes et al. . |
| 4,673,405 | 6/1987 | Guittard et al. . |
| 4,678,467 | 7/1987 | Eckenhoff et al. . |
| 4,705,515 | 11/1987 | Wong et al. . |
| 5,131,994 * | 7/1992 | Shmidt et al. ..................... 204/180.1 |
| 5,158,537 | 10/1992 | Haak et al. . |
| 5,198,229 | 3/1993 | Wong et al. . |
| 5,288,289 | 2/1994 | Haak et al. . |
| 5,320,598 | 6/1994 | Haak et al. . |
| 5,385,543 | 1/1995 | Haak et al. . |
| 5,413,572 | 5/1995 | Wong et al. . |
| 5,443,459 | 8/1995 | Wong et al. . |
| 5,499,979 | 3/1996 | Wong et al. . |
| 5,643,207 | 7/1997 | Rise . |
| 5,773,019 | 6/1998 | Ashton et al. . |

* cited by examiner

Primary Examiner—Richard K. Seidel
Assistant Examiner—Michael J. Hayes
(74) Attorney, Agent, or Firm—Banner & Witcoff, Ltd.

(57) ABSTRACT

A drug delivery system recirculate carrier fluid in closed-loop fashion, thereby requiring only a relatively small amount of carrier fluid for operation. A pump provides continuous flow of carrier fluid to a delivery interface in a recirculating path. A metering device, which may be either passive or active, dispenses drug from a reservoir into the carrier fluid in the recirculating path and maintains a constant concentration of drug at the delivery interface, which may comprise a semipermeable membrane. The recirculating path is preferably in the form of a dual-lumen catheter which provides a supply leg to a delivery interface and a return leg from the drug delivery interface to the pump. Drug concentration sensors may be provided to measure the concentration of drug in the recirculating path or in the human body and to actively adjust the metering device accordingly.

17 Claims, 2 Drawing Sheets

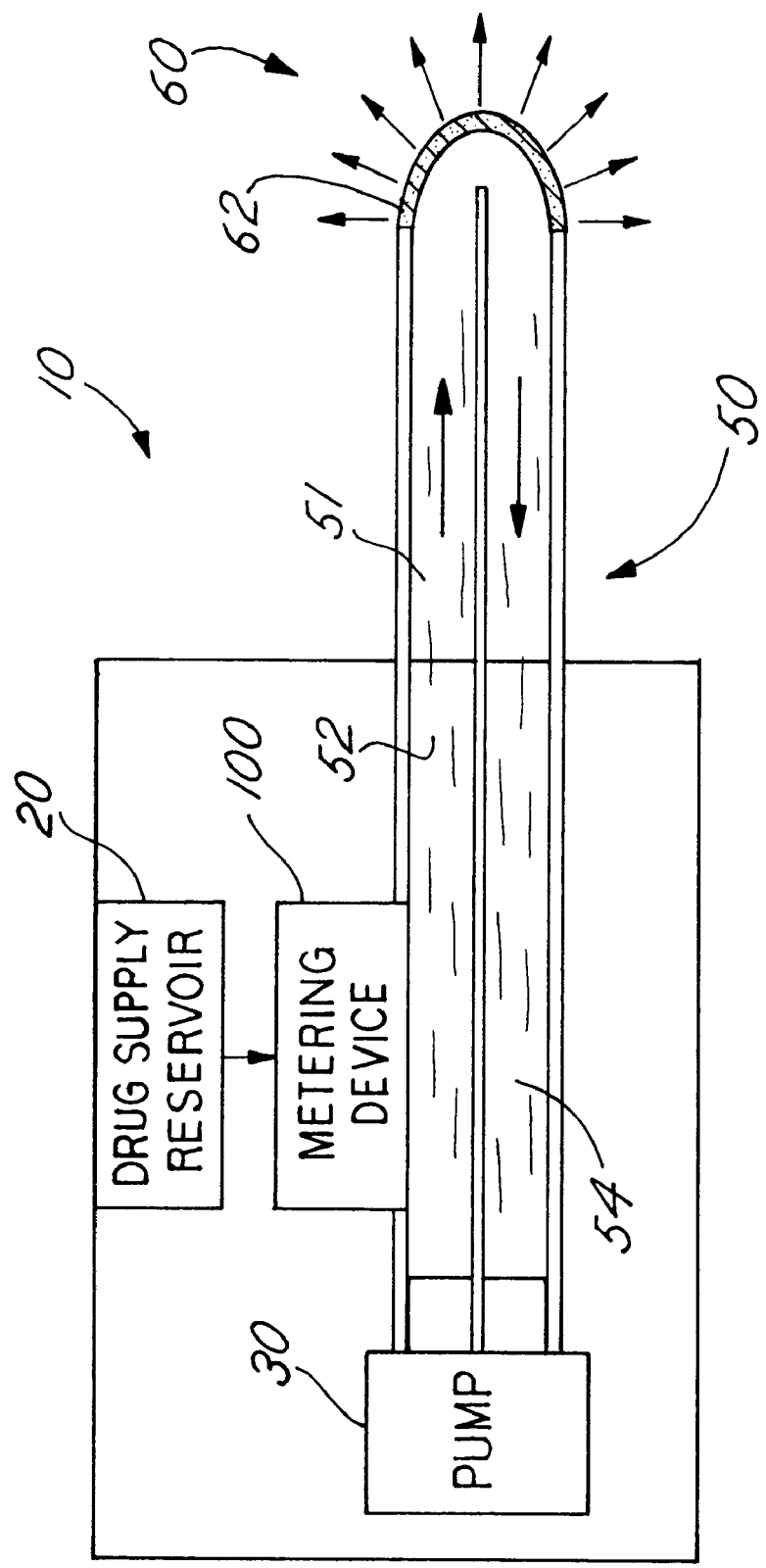

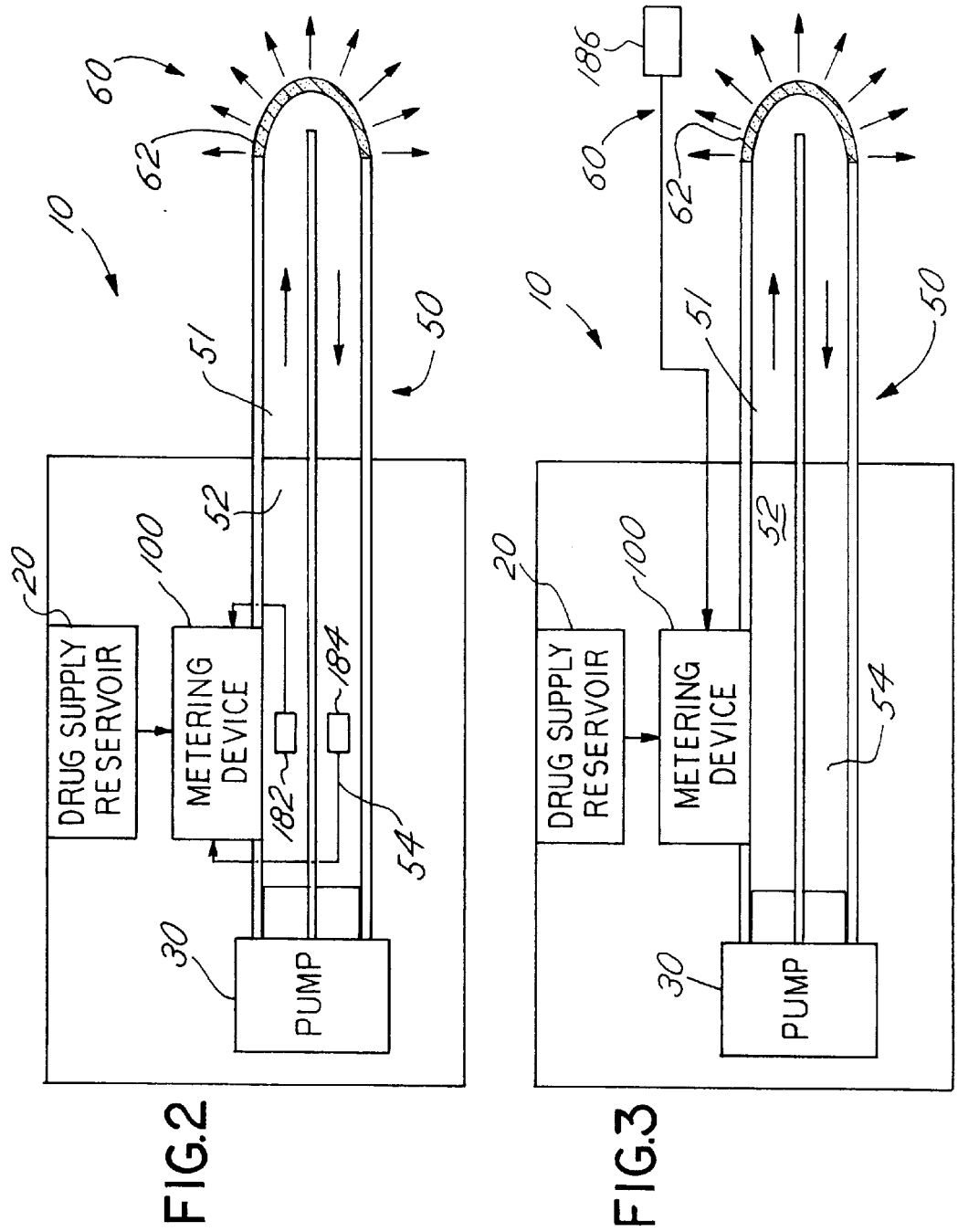

RECIRCULATING IMPLANTABLE DRUG DELIVERY SYSTEM

BACKGROUND OF THE INVENTION

1. Field of the Invention

The present invention relates generally to methods and apparatus for delivering drug therapy to the human body. More particularly, the invention relates to implantable apparatus and methods for delivering drug therapy using a recirculating carrier fluid.

2. Description of the Related Art

In conventional implantable drug delivery devices, drug is dissolved in a carrier fluid and the drug/carrier fluid combination is stored in a reservoir and a closely controlled dosage metered and delivered to the body. Drug concentration in the carrier fluid is typically kept very low. One reason for this is that many drugs become unstable at higher concentrations or may precipitate out of the carrier fluid, resulting in blockage within the delivery device. Another reason is that high concentrations of drug may lead to local toxic effects during delivery and would require very low infusion rates beyond the controllable range of many delivery devices. Also, inadvertent leakage of carrier fluid bearing large concentrations of drug would present a danger to the human body.

Since the concentration of drug in the carrier fluid is typically very low, often on the order of a few micrograms to a few milligrams per milliliter of carrier, relatively large volumes of carrier fluid must be stored within the implantable drug delivery device and periodically replenished by refilling from sources external to the human body. For example, in the SYNCHROMED® infusion pump, manufactured by Medtronic, Inc. of Minneapolis, Minnesota, at least half of the total device volume is occupied by the pump reservoir, which stores carrier and drug. In a morphine administering application, morphine sulfate is dissolved in water at a concentration of less than 50 milligrams per milliliter. Thus, less than 5-percent of the fluid stored in the pump reservoir is actually active drug. In prior art devices, further reduction of the pump size, although desirable, is not achievable without corresponding loss in drug storage capacity.

Some known systems, such as the one disclosed in U.S. Pat. No. 5,643,207, have utilized endogenous body fluids as carrier fluids in order to provide more compact delivery devices. However, such systems present difficulties in controlling the concentration of drug in the physiological fluids and, due to the chemical make-up of physiological fluids, are limited in the types of drug that may be delivered using such systems. There is thus a need for a drug delivery system which eliminates the need for large storage capacity yet which is capable of extended delivery without refilling.

SUMMARY OF THE INVENTION

The aforementioned problems are solved by the invention which provides a drug delivery system which recirculates the carrier fluid in closed-loop fashion, thereby requiring only a relatively small amount of carrier fluid for operation. In a preferred embodiment, the invention provides a drug reservoir and a pump which provides carrier fluid to a recirculating path. The recirculating path is preferably in the form of a dual-lumen catheter which provides a supply leg to a drug delivery interface and a return leg from the drug delivery interface to the pump. A metering device maintains the concentration of drug within the supply leg of the recirculating path. A drug delivery interface is provided between the recirculating path and the living body in the form of a semi-permeable membrane which permits a flow of drug from the recirculating path, yet which prevents a net outflow of carrier fluid from the recirculating path. In another preferred embodiment, drug concentration sensors are provided to measure the concentration of drug in the recirculating path or in the human body and to actively adjust the metering device accordingly.

A primary advantage of the present invention is that rate of drug infusion through the drug delivery interface is a function of the difference in concentration across the interface; the rate of drug infusion is substantially independent of the flow rate of fluid through the recirculation path.

BRIEF DESCRIPTION OF THE DRAWINGS

The invention will be described with reference to the drawings, which form a part of this specification. Those of ordinary skill will understand that the invention is not intended to be limited to these exemplary embodiments illustrated in the drawings, of which:

FIG. 1 is a schematic illustration of a recirculating drug infusion system according to a preferred embodiment of the present invention;

FIG. 2 is a schematic illustration of a recirculating drug infusion system according to another preferred embodiment of the invention;

FIG. 3 is a schematic illustration of a recirculating drug infusion system according to another preferred embodiment of the invention.

DETAILED DESCRIPTION OF THE INVENTION

Referring to FIG. 1, a drug delivery device 10 according to a preferred embodiment of the present invention comprises generally a drug supply reservoir 20, a recirculating path 50 containing a carrier fluid 52, drug metering device 100, and a drug delivery interface 60. Each of these components will be described in more detail below.

Drug supply reservoir 20 is preferably provided in the form of a pressurized reservoir, which may comprise, for example, a bellows assembly and refill components like those described in U.S. Pat. No. 5,643,207, the subject matter of which is incorporated herein by reference in its entirety. As used herein, the terms "drug reservoir" and "drug supply reservoir" are intended to refer to containers or reservoirs capable of containing drugs, medicaments or therapeutic agents. Recirculating path 50 is preferably provided as a dual-lumen catheter which is constructed of a non-permeable polymer and which is provided at its tip with a semi-permeable membrane 62 forming the drug delivery interface 60. Dual-lumen catheter includes a supply leg 51 for conveying carrier fluid from the pump 30 to the drug delivery interface 60, and a return leg 54 for conveying carrier fluid from the drug delivery interface 60 to the pump 30. Semipermeable membrane 62 is preferably comprised of a polymeric substance. The permeability of membrane 62 is preferably selected to permit diffusion of drug from the carrier fluid 52 to the living body, as represented by the arrows in FIG. 1. It will be recognized that an outer surface of membrane 62 must be exposed to a body fluid, preferably a body fluid that is flowing so as to distribute drug that has diffused through membrane 62 to the body. It will be apparent to those of ordinary skill that it is a gradient in drug concentration across the semipermeable membrane 62 that results in the diffusion of drug from the catheter tip. For example, water from the body and carrier fluid may pass through the membrane 62 in both directions, but there will be no net transfer of fluid across the membrane because there is no net concentration gradient. As an alternative embodiment, drug delivery interface 60 may be provided as an iontophoretic delivery interface which utilizes an anode and cathode to create an electric field for promoting the migration of drug ions from the recirculating path 50.

Drug metering device 100 functions to maintain the concentration of drug in the carrier fluid 52 within the supply leg 51 and therefore the concentration of drug at the drug delivery interface 60. Metering device 100 may be either active or passive. For example, a passive metering device may be provided as another permeable membrane, one side of which is exposed to the drug, in powder form or high concentration liquid form and another side of which is exposed to the carrier fluid 52. Such a permeable membrane would permit maintenance of a predetermined concentration of drug within the carrier fluid passing over the membrane.

An active drug metering device may be provided in the form of a pump or valve for providing a metered supply of drug into the carrier fluid. Such an active metering device may comprise, for example, a micromachined pump or valve such as those disclosed in U.S. Pat. No. 5,839,467, the subject matter of which is incorporated herein, in its entirety, by reference. Exemplary pumps are also described by B. T. G. van Lintel et al. in "a Piezoelectric Micropump Based on Micromachining of Silicon," 15 Sensors and Actuators 153–163 (1988) and by Jan G. Smits in "Piezoelectric Micropump with Three Valves Working Peristaltically," A21–A23 Sensors and Actuators 203–206 (1990). An exemplary valve is described by T. Ohnstein et al. in "Microinachinied Silicon Microvalve," Proceedings, IEEE, Micro Electro Mechanical Systems, Napa Valley, Calif., pages 95–98 (Feb. 11–14, 1990). Such valves or pumps may be controlled by appropriate circuitry to release controlled amounts of drug into the carrier fluid in order to maintain a desired concentration of drug in the carrier fluid in the supply leg 51.

In operation, the pump 30 provides a continuous flow of carrier fluid 58 through the recirculating path 50. The drug metering device 100 substantially maintains a constant predetermined concentration of drug in the carrier fluid 52 and therefore at the drug delivery interface 60. As carrier fluid 52 is circulated along the supply leg of the recirculating path 50, it encounters the drug delivery interface 60, which permits the migration of drug from the recirculating path 50 to the living body. The concentration of drug within the carrier fluid 52 passing within the drug delivery interface 60 is thereby reduced as the carrier fluid 52 passes through the drug delivery interface 60. As the reduced-concentration carrier fluid is recirculated to the metering device 100, via return leg 54 and pump 30, the drug concentration within the carrier fluid is increased to the predetermined level.

Referring now to FIG. 2, according to a primary feature of the invention, an active drug metering device 100 may be provided with one or more sensors 182, 184 for sensing the concentration of drug in the carrier fluid 52 and controlling the metering of drug using feedback or closed-loop control techniques. For this purpose, suitable control circuitry would be incorporated into the metering device, for example, a microprocessor based computer which is programmed to interpret signals provided to it from the sensors. A supply leg sensor 182 is provided for sensing the concentration of drug in the carrier fluid 52 in the supply leg 51. Similarly, a return leg sensor 184 is provided for sensing the concentration of drug in the carrier fluid 52 in the return leg 54. Signals representing the concentration of drug in the supply leg and the return leg 54 are conveyed via appropriate conductors to the control circuitry in the metering device 100. The difference between the sensed concentration of drug in the supply leg and the sensed concentration in the return leg 54 would provide an indication of the amount of drug diffused through the delivery interface 60.

Referring now to FIG. 3, an alternative embodiment of the present invention includes a single sensor 186 which is disposed external to the recirculating path 50 so as to sense the concentration of drug in the living body at or near the drug delivery interface 60. Signals from the sensor 186 may be processed by appropriate circuitry as described above.

Although preferred embodiments of this invention have been described above in some detail, it should be appreciated that a variety of embodiments will be readily apparent from the foregoing description to persons of ordinary skill. The description is intended to be illustrative of the preferred embodiment of this invention and not intended to be limiting to the scope of protection sought by the applicants, which scope is defined by the appended claims.

What is claimed is:

1. A system for delivering drug therapy to a living body, comprising:
    a) a drug reservoir for containing a supply of drug;
    b) a recirculating closed loop carrier path including a carrier fluid contained therein, the recirculating carrier path connected to the drug reservoir;
    c) a metering device for introducing drug from the drug reservoir into the carrier fluid to substantially maintain a predetermined concentration of drug in the carrier fluid, the metering device operatively connected to the drug reservoir; and
    d) a delivery interface located on the recirculating carrier path for permitting controlled passage of the drug from the carrier fluid to the human body.

2. The system of claim 1, wherein the metering device comprises a passive metering device.

3. The system of claim 1, wherein the metering device comprises an active metering device.

4. The system of claim 1, wherein the recirculating carrier path includes a dual-lumen catheter having a supply leg and a return leg, and a pump in fluid communication with the dual-lumen catheter to pump the carrier fluid from the return leg to the supply leg.

5. The system of claim 1, wherein the drug is provided in powder form.

6. The system of claim 1, wherein the metering device further comprises at least one sensor for sensing the concentration of drug in the carrier fluid.

7. The system of claim 1, wherein the metering device further comprises a sensor for sensing the concentration of drug in the living body.

8. The system of claim 1, wherein the delivery interface comprises a semi-permeable membrane adapted to permit migration of drug into the living body while preventing a net migration of the carrier fluid out of the recirculating path.

9. The system of claim 1, wherein the delivery interface comprises an iontophoretic system for creating an electric field to assist in the migration of drug from the recirculating path into the living body.

10. A method of delivering a beneficial agent to a living body, the method comprising the steps of:
    a) providing a recirculating closed-loop path of carrier fluid;

b) providing a drug delivery interface in communication with the carrier fluid; and c) metering drug into the carrier fluid in the recirculating closed-loop path.

11. The method of claim 10, further comprising the step of substantially maintaining a predetermined concentration of drug in the carrier fluid at the delivery interface.

12. The method of claim 10, wherein the step of metering drug further comprises the step of actively metering drug.

13. The method of claim 10, wherein the step of metering drug further comprises the step of passively metering drug.

14. The method of claim 10, wherein the step of metering drug further comprises the step of sensing the concentration of drug in the recirculating path.

15. A system for delivering drug therapy to a living body, comprising:

a) a drug reservoir for containing a supply of drug;

b) a recirculating closed-loop carrier path including a dual-lumen catheter having a supply leg and a return leg and carrier fluid contained therein, the recirculating carrier path connected to the drug reservoir;

c) a metering device operatively connected to the drug reservoir for introducing drug from the drug reservoir into the carrier fluid to substantially maintain a predetermined concentration of drug in the carrier fluid, the metering device including at least one sensor for sensing the concentration of drug in the carrier fluid;

d) a delivery interface located on the recirculating carrier path for permitting controlled passage of the drug from the carrier fluid to the human body, including a semi-permeable membrane adapted to permit migration of drug into the living body while preventing a net migration of the carrier fluid out of the recirculating path; and e) a pump in fluid communication with the dual-lumen catheter to pump the carrier fluid from the return leg to the supply leg.

16. A method of delivering a beneficial agent to a living body, the method comprising the steps of:

a) providing a recirculating closed-loop path of carrier fluid;

b) providing a drug delivery interface in communication with the carrier fluid; and c) actively metering drug into the carrier fluid in the recirculating closed-loop path by sensing the concentration of drug in the recirculating path to substantially maintain a predetermined concentration of drug in the carrier fluid at the delivery interface.

17. A method of delivering a beneficial agent to a living body, the method comprising the steps of:

a) providing a recirculating closed-loop path of carrier fluid;

b) providing a drug delivery interface in communication with the carrier fluid; and c) passively metering drug into the carrier fluid in the recirculating closed-loop path to substantially maintain a predetermined concentration of drug in the carrier fluid at the delivery interface.

* * * * *